United States Patent
Lilja et al.

(10) Patent No.: US 9,662,425 B2
(45) Date of Patent: May 30, 2017

(54) METHOD FOR DRUG LOADING HYDROXYAPATITE COATED IMPLANT SURFACES

(71) Applicant: Stryker European Holdings I, LLC, Kalamazoo, MI (US)

(72) Inventors: Mirjam Lilja, Farsta (SE); Jan Henrik Sörensen, Kiel (DE); Philip Procter, Divonne les Bains (FR); Hartwig Steckel, Kiel (DE); Torben Christian Sörensen, Mönkeberg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/786,060

(22) PCT Filed: Apr. 22, 2014

(86) PCT No.: PCT/IB2014/060905
§ 371 (c)(1),
(2) Date: Oct. 21, 2015

(87) PCT Pub. No.: WO2014/174437
PCT Pub. Date: Oct. 30, 2014

(65) Prior Publication Data
US 2016/0058922 A1    Mar. 3, 2016

Related U.S. Application Data

(60) Provisional application No. 61/814,538, filed on Apr. 22, 2013.

(51) Int. Cl.
*A61L 27/32* (2006.01)
*A61L 31/16* (2006.01)
(Continued)

(52) U.S. Cl.
CPC .......... *A61L 31/16* (2013.01); *A61C 8/0013* (2013.01); *A61C 19/063* (2013.01); *A61L 27/32* (2013.01);
(Continued)

(58) Field of Classification Search
CPC .............................. A61L 27/32; B05D 3/0218
(Continued)

(56) References Cited

U.S. PATENT DOCUMENTS 5,047,034 A    9/1991 Sohngen
5,053,212 A    10/1991 Constantz et al.
(Continued)

FOREIGN PATENT DOCUMENTS

CN     101537208 A    9/2009
EP     0806212 A1     11/1997
(Continued)

OTHER PUBLICATIONS

Brohede et al. Multifunctional implant coatings providing possibilities for fast antibiotics loading with subsequent slow release. J. Materials Science: Materials Medicine (2009) 20:1859-1867.*
(Continued)

*Primary Examiner* — Cachet Sellman
(74) *Attorney, Agent, or Firm* — Lerner, David, Littenberg, Krumholz & Mentlik, LLP

(57) ABSTRACT

A method for loading a hydroxyapatite coated implant with a therapeutic agent including the steps of providing an implant and applying a hydroxyapatite coating on a surface of the implant. The hydroxyapatite coated implant is contacted with a solution including the therapeutic agent. The hydroxyapatite coated implant and solution is heated to temperature of about 60° C. to about 100° C. Pressure is applied to the hydroxyapatite coated implant and solution from about 2 bar to about 10 bar, to load the hydroxyapatite
(Continued)

coated implant with the therapeutic agent. An implant made according to the method has sustained therapeutic agent delivery and includes a base and a biomimetic hydroxyapatite coating disposed on a surface thereof.

21 Claims, 14 Drawing Sheets

(51) Int. Cl.
    *A61C 8/00*     (2006.01)
    *A61L 27/54*     (2006.01)
    *A61L 31/08*     (2006.01)
    *A61C 19/06*     (2006.01)
    *C23C 4/12*     (2016.01)
(52) U.S. Cl.
    CPC .............. *A61L 27/54* (2013.01); *A61L 31/086* (2013.01); *C23C 4/127* (2013.01)
(58) Field of Classification Search
    USPC .............................................. 427/2.24, 2.27
    See application file for complete search history.

(56) References Cited

U.S. PATENT DOCUMENTS

| | | |
|---|---|---|
| 5,164,187 A | 11/1992 | Constantz et al. |
| 5,188,670 A | 2/1993 | Constantz |
| 5,279,831 A | 1/1994 | Constantz et al. |
| 5,964,932 A | 10/1999 | Ison et al. |
| 5,968,253 A | 10/1999 | Poser et al. |
| 6,053,970 A | 4/2000 | Ison et al. |
| 6,558,709 B2 | 5/2003 | Higham |
| 6,596,338 B2 | 7/2003 | Scott et al. |
| 6,821,528 B2 | 11/2004 | Scott et al. |
| 2003/0049324 A1 | 3/2003 | Vogt et al. |
| 2003/0077381 A1* | 4/2003 | Scott ................. A61L 27/32 427/2.24 |
| 2006/0134160 A1 | 6/2006 | Troczynski et al. |
| 2007/0213832 A1 | 9/2007 | Wen |
| 2007/0259101 A1* | 11/2007 | Kleiner ............... A61L 27/30 427/2.24 |
| 2008/0306579 A1* | 12/2008 | Dolan ................. A61F 2/91 623/1.11 |
| 2009/0269480 A1 | 10/2009 | Berglund |

FOREIGN PATENT DOCUMENTS

| | | | | |
|---|---|---|---|---|
| SE | WO 2010126436 A1 * | 11/2010 | ............. A61L 27/32 |
| WO | 2009100792 A2 | 8/2009 | | |
| WO | 2013013218 A2 | 1/2013 | | |
| WO | 2013067049 A1 | 5/2013 | | |
| WO | 2013072576 A1 | 5/2013 | | |

OTHER PUBLICATIONS

Ulrika Brohede et al: "Multifunctional implant coatings providing possibilities for fast antibiotics loading with subsequent slow release", Journal of Materials Science: Materials in Medicine, Kluwer Academic Publishers, BO, vol. 20, No. 9, Apr. 28, 2009 (Apr. 28, 2009) pp. 1859-1867, XP019730963, ISSN: 1573-4838, DOI: 10.1007/S10856-009-3749-6 cited in the application the whole document in particular: p. 1861, left-hand column, last paragraph and p. 1866, last paragraph.
Stigter M et al: "Incorporation of tobramycin into biomimetic hydroxyapatite coating on titanium", Biomaterials. Elsevier Science Publishers BV., Barking, GB, vol. 23, No. 20, Oct. 1, 2002 (Oct. 1, 2002), pp. 4143-4153. XP004370405, ISSN: 0142-9612. DOI: 10.1016/S0142-9612(02)00157-6 cited in the application abstract page 4145, left-hand column, last paragraph-right-hand column, paragraph 2 p. 4153, last paragraph.
Stigter M et al: "Incorporation of different antibiotics into carbonated hydroxyapatite coatings on titanium implants. release and antibiotic efficacy", Journal of Controlled Release, Elsevier, Amsterdam, NL, vol. 99, No. 1, Sep. 14, 2004 (Sep. 14, 2004). pp. 127-137, XP004549075, ISSN: 0168-3659. DOI: 10.1016/J. JCONREL.2004.06.011 abstract p. 128, right-hand column, paragraph 2-p. 129, left-hand column, paragraph 1, p. 136, last paragraph.
International Search Report for Application No. PCT/IB2014/060905 dated Jun. 26, 2014.
"Non-Toxic and Bio-Compatible Type 2 Titanium Anodizing", 2003, XP055117504, Retrieved from the Internet: <URL: hittp://www.danco.net/PDF-DOWNLOADS/TITANIUM I I. pdf>, [retrieved on May 12, 2014].
Aberg et al, Bisphosphonate incorporation in surgical implant coatings by fast loading and co-precipitation at low drug concentrations, J Mater Sci: Mater Med (2009) 20:2053-2061.
Abtahl et al, A bisphosphonate-coating improves the fixation of metal implants in human bone, a randomized trial of dental implants, Bone 50 (2012) 1148-1151.
Brohede et al, Multifunctional implant coatings providing possibilities for fast antibiotics loading with subsequent slow release, J Mater Sci: Mater Med (2009) 20:1859-1867.
Brunski et al, Biomaterials and Biomechanics of Oral and Maxillofacial Implants: Current Status and Future Developments, The Inrternational Journal of Oral & Maxillofacial Implants, 2000. 15-46.
F. Chai et al, Antibacterial activation of hydroxyapatite (HA) with controlled porosity by different antibiotics, Biomolecular Engineering 24 (2007) 510-514.
Forsgren et al, Co-loading of bisphosphonates and antibiotics to a biomimetic hydroxyapatite coating, Biotechnol Lett (2011) 33 :1265-1268.
Hetrick et al, Reducing implant-related infections: active release strategies, I Chem. Soc. Rev., 2006, 35, 780-789.
Hutson et al, Infections in Periarticular Fractures of the Lower Extremity Treated with Tensioned Wire Hybrid Fixators, Journal of Orthopaedic Trauma vol. 12, No. 3, 1998, pp. 214-218.
International Search Report for Application No. PCT/EP2013/068082 dated May 26, 2014.
International Search Report for Application No. PCT/IB2014/062454 dated Sep. 29, 2014.
James M Anderson, Biological Responses to Materials, Annu. Rev. Mater. Res. 2001. 31:81-110.
Johan Forsgren et al, Formation and adhesion of biomimetic hydroxyapatite deposited on titanium substrates, Acta Eliomaterialia 3 (2007) 980-984.
K.C. Baker et al, Growth, characterization and biocompatibility of bone-like calcium phosphate layers biomimetically deposited on metallic substrata, Materials Science and Engineering C 26 (2006) 1351-1360.
Lilja et al, Photocatalytic and antimicrobial properties of surgical implant coatings of titanium dioxide deposited though cathodic arc evaporation, Biotechnol Lett (2012) 34:2299-2305.
Liu et al, Water-based sol-gel synthesis ofhydroxyapatite: process development, Biomaterials 22 (2001) 1721-1730.
M.P. Ginebra et al, Calcium phosphate cements as bone drug delivery systems: A review, Journal of Controlled Release 113 (2006) 102-110.
Ma et al, Electrophoretic deposition of porous hydroxyapatite scaffold, Biomaterials 24 (2003) 3505-3510.
Mahan et al, Factors in Pin Tract Infections, Department of Orthopedic Surgery, University of Louisville, Louisville, Ky., Mar. 1991 vol. 14 No. 3 V , pp. 305-308.
Masse et al, Prevention of Pin Track Infection in External Fixation with Silver Coated Pins: Clinical and Microbiological Results, J Biomed Mater Res (Appl Biomater) 53: 600-604, 2000.
Poelstra et al, Prophylactic treatment of gram-positive and gram-negative abdominal implant infections using locally delivered polyclonal antibodies, Received: Jun. 15, 2000, pp. 206-215.
Sergio Allegrini Jr., et al, Hydroxyapatite grafting promotes new bone formation and osseointegration of smooth titanium implants, Ann Anat 188 (2006) 143-151.

(56) References Cited

OTHER PUBLICATIONS

Tengvalla et al, Surface immobilized bisphosphonate improves stainless-steel screw fixation in rats, Biomaterials 25 (2004) 2133-2138.
Zilberman et al, Antibiotic-eluting medical devices for various applications, journal of Controlled Release 130 (2008) 202-215.
Sörensen et al., "Biomechanical and antibacterial properties of Tobramycin loaded hydroxyapatite coated fixation pins", Journal of Biomedical Materials Research B: Applied Biomaterials, 2014, vol. 00B, Issue 00, 12 pages.
Sörensen et al., "Biomimetic Hydroxyapatite Coated Titanium Screws Demonstrate Rapid Implant Stabilization and Safe Removal In-Vivo", Journal of Biomaterials and Nanobiotechnology, 2015, 6, 20-35.

\* cited by examiner

METHOD FOR DRUG LOADING HYDROXYAPATITE COATED IMPLANT SURFACES

CROSS-REFERENCE TO RELATED APPLICATIONS

The present application is a national phase entry under 35 U.S.C. §371 of International Application No. PCT/IB2014/060905 filed Apr. 22, 2014, published in English, which claims priority from U.S. Patent Application No. 61/814,538 filed Apr. 22, 2013, all of which are hereby incorporated herein by reference.

TECHNICAL FIELD AND INDUSTRIAL APPLICABILITY

The present disclosure relates to a method for adsorptive loading of a therapeutic agent to a hydroxyapatite coated implant, and more particularly, to a loading procedure using a solution temperature of about 60° C. to about 100° C. and a pressure of about 2 bar to about 10 bar, and an implant with sustained therapeutic drug delivery.

BACKGROUND

External fixation pins are commonly used to stabilize orthopedic injuries and are considered to be fast and minimally invasive tools to allow for easy reduction of fractures. Despite the promising advantages with respect to damage control in orthopedics, pin tract infection and pin loosening are frequently occurring complications of external fixations.

Due to the contact with external skin layers, fixation pins may act as gateways for bacteria. Reported infection rates for external fixator fracture treatments range from 0.5% up to 50% and often cause bone loss, resulting in a decreased pin-bone interface. See Hutson J. J. et al., "Infections in Periarticular Fractures of the Lower Extermity Treated with Tensioned Wire Hybrid Fixators"*J Orthop Trauma* 12 214-218 (1998); Mahan j. et al. "Factors in Pin Tract Infections" *Orthopedics* 14 305-308 (1991); and Masse A. et al., "Prevention of Pin Track Infection in External Fixation with Silver Coated Pins: Clinical and Microbiological Results" *J Biomed Mater Res* 53 600-604 (2000). Conversely, instability of the pin-bone construct can lead to pin loosening and further infection. Thus, inhibiting bacterial adhesion may be seen as the most critical step in preventing implant associated infections. See Brunski J. B. et al., "Biomaterials and Biomechanics of Oral and Maxillofacial Implants: Current Status and Future Developments" *Int J Oral Max Impl* 15 15-46 (2000) and Hetrick E. M. et al., "Reducing Implant Related Infections: Active Release Strategies" *Chem Soc Rev* 35 780-789 (2006).

In order to overcome the poor accessibility of the bone-infected site by systematically administered antibiotics, many researchers have attempted to reduce infections at the bone-pin interface by designing functional surface coatings for local drug administration. See Brohede U. et al., "Multifunctional Implant Coatings Providing Possibilities For Fast Antibiotics Loading with Subsequent Slow Release"*J Mater Sci Mater Med* 20 1859-1867 (2009), the entirety of which is hereby incorporated by reference.

The major advantage of local antibiotics delivery compared to conventional systemic delivery for both infection prevention and treatment is that high local doses of antibiotics against specific pathogens associated with implant infection can be administered without reaching systemic toxicity levels of the drug itself. However, the effectiveness of antibiotics-loaded implant coatings is strongly dependent on the rate and manner in which the drug is released.

If the antibiotics are released at levels below the minimum inhibition concentration (MIC), bacterial resistance may be induced at the release sit. A six hour post implantation "decisive period" during which the prevention of bacterial adhesion is critical to the long-term success of the implant has been identified. See Poelstra K. A. et al., "Prophylactic Treatment of Gram-positive and Gram-negative Abdominal Implant Infections Using Locally Delivered Polyclonal Antibodies"*J Biomed Mater Res* 60 206-215 (2002). Thus, an optimum local antibiotic release profile for orthopedic implants should feature a high initial release rate during the first hours after implantation, followed by a sustained release to inhibit the occurrence of latent infection and allow for protective fibrous capsule formation as well as tissue integration. See Zilbermann M. et al., "Antibiotic-eluting Medical Devices for Various Applications" *J Control Release* 120 202-215 (2008) and Anderson J. H. "Biological Responses to Materials" *Annu Rev Mater Res* 31 81-110 (2001).

Bioactive ceramics and ceramic coatings have been investigated by several researchers as drug delivery vehicles for transport and sustained release of antibiotics. Hydroxyapatite (HA) is widely used in orthopedic surgery due to its excellent osteoconductive properties. Numerous techniques are known for coating implants with HA, including plasma spraying, dip coating, sputter deposition, electrophoretic deposition and sol-gel synthesis. The biomimetic method of HA coating requires soaking the implant in a simulated body fluid at an appropriate temperature and pH. Plasma sprayed HA coatings on implant surfaces have demonstrated a high clinical success rate based on greater bone-pin contact, enhanced bone-integration and long term fixation. Nevertheless, incorporating drugs into a plasma sprayed HA coating during deposition is not feasible due to the high process temperatures of the plasma flame.

Biomimetically deposited HA coatings offer a straightforward approach to prepare implant coatings at low process temperature having good adhesion, as well as step coverage. Implant surfaces functionalized with a hydroxyapatite (HA) coating contribute towards an enhanced bone bonding capability and increases bone in-growth towards the implant surface. In addition, such HA coatings have shown promising potential to be used as a drug vehicle for local drug delivery at the implantation site. The nanoporous structure of such HA coatings allow loading antibiotics by a simple soaking procedure and it has been shown that it is possible to incorporate growth factors to promote tissue healing as well as to co-load growth-factors and antibiotics into the HA-matrix.

Even if biomimetic HA-coatings appear to be promising vehicles for local administration of antibiotics, the longest antibacterial effect demonstrated till date using this approach does not exceed three days. Chai F. et al., "Antibacterial Activation of Hydroxyapatite (HA) with Controlled Porosity by Different Antibiotics" *Biomol Eng* 24 510-514 (2007). Thus, a major challenge related to antibiotic-loaded HA coatings lies in increasing the action time of the antibiotics at the implant site.

Another well documented challenge is that native amorphous $TiO_2$ has very poor ability to let HA form on its surface through biomimetic precipitation from a solution, whereas HA crystallizes spontaneously on the crystalline anatase and rutile phases of $TiO_2$ when soaked in simulated body fluid.

SUMMARY

According to one aspect of the present disclosure a method for loading a hydroxyapatite coated implant with a therapeutic agent includes the steps of providing an implant and applying a hydroxyapatite coating on a surface of the implant. The hydroxyapatite coated implant is contacted with a solution including the therapeutic agent. The hydroxyapatite coated implant and solution is heated to temperature of about 60° C. to about 100° C. Pressure is applied to the hydroxyapatite coated implant and solution from about 2 bar to about 10 bar, to load the hydroxyapatite coated implant with the therapeutic agent.

In another aspect, a method for loading an implant with a therapeutic agent includes the steps of providing an implant and applying a biomimetic hydroxyapatite coating on a surface of the implant. The implant is loaded with a therapeutic agent by heating the hydroxyapatite coated implant and solution of therapeutic agent and applying pressure to the hydroxyapatite coated implant and solution for improved therapeutic agent deposition.

In yet another aspect, an implant having sustained therapeutic agent delivery includes a base and an hydroxyapatite coating disposed on a surface of the base. The hydroxyapatite coating includes a therapeutic agent, wherein the therapeutic agent is loaded in the hydroxyapatite coating by heating the hydroxyapatite coated base in a solution of therapeutic agent to a temperature of about 60° C. to about 100° C. and applying pressure of about 2 to about 10 bar to the hydroxyapatite coated base and solution for improved therapeutic agent deposition.

These and other objects, features, aspects, and advantages of the present disclosure will become more apparent from the following detailed description of the preferred embodiment relative to the accompanied drawings, in which:

BRIEF DESCRIPTION OF THE DRAWINGS

FIGS. 5(a)-(d) are SEM images of ion milled cross-sections of HA-B coatings (FIGS. 5(a) and 5(b)) and HA-P (FIGS. 5(c) and 5(d)) coatings deposited on fixation pins.

DETAILED DESCRIPTION

As fully set forth herein, the present disclosure provides a methodology for adsorptive loading of a therapeutic agent to a hydroxyapatite coated implant, wherein an increased temperature of the PBS solution is used, for example, about 70° C. to about 100° C., instead of soaking at room temperature. In connection with this increased temperature an applied elevated pressure of, for example, about 4-8 bar, during the loading procedure is used. The viscosity of the antibiotic containing loading solution decreases with increased temperature and at the same time the antibiotic diffusion coefficient increases, which in combination with elevated pressure results in an increased penetration depth of the drugs into the coating structure.

Drug, pharmaceutical or therapeutic agent, as used herein, refers to, but in no way is limited to, antibiotics, vitamins, chemotherapy drugs, bisphosphonates, strontium-ranelate, PTH, osteoporotic drugs, growth factors, or a combination thereof.

"Implant Device", "implant/device" and the like are used synonymously to refer to any object that is designed to be placed partially or wholly within a patient's body for one or more therapeutic purposes such as for restoring physiological function, alleviating symptoms associated with disease, delivering therapeutic agents, and/or repairing or replacing or augmenting etc. damaged or diseased organs and tissues.

Representative examples of medical implants/devices include pins, fixation pins and other orthopedic devices, dental implants, stents, balloons, drug delivery devices, sheets, films and meshes, soft tissue implants, implantable electrodes, implantable sensors, drug delivery pumps, tissue barriers and shunts. It should be appreciated that other devices listed herein are contemplated by the present disclosure.

Representative materials for the implant include, but are not limited to, metals and metal alloys (e.g., titanium, titanium alloy, nickel-titanium alloy, tantalum, platinum-iridium alloy, gold, magnesium, stainless steel, chromo-cobalt alloy); ceramics; and biocompatible plastics or polymers and combinations thereof.

Figure 1:
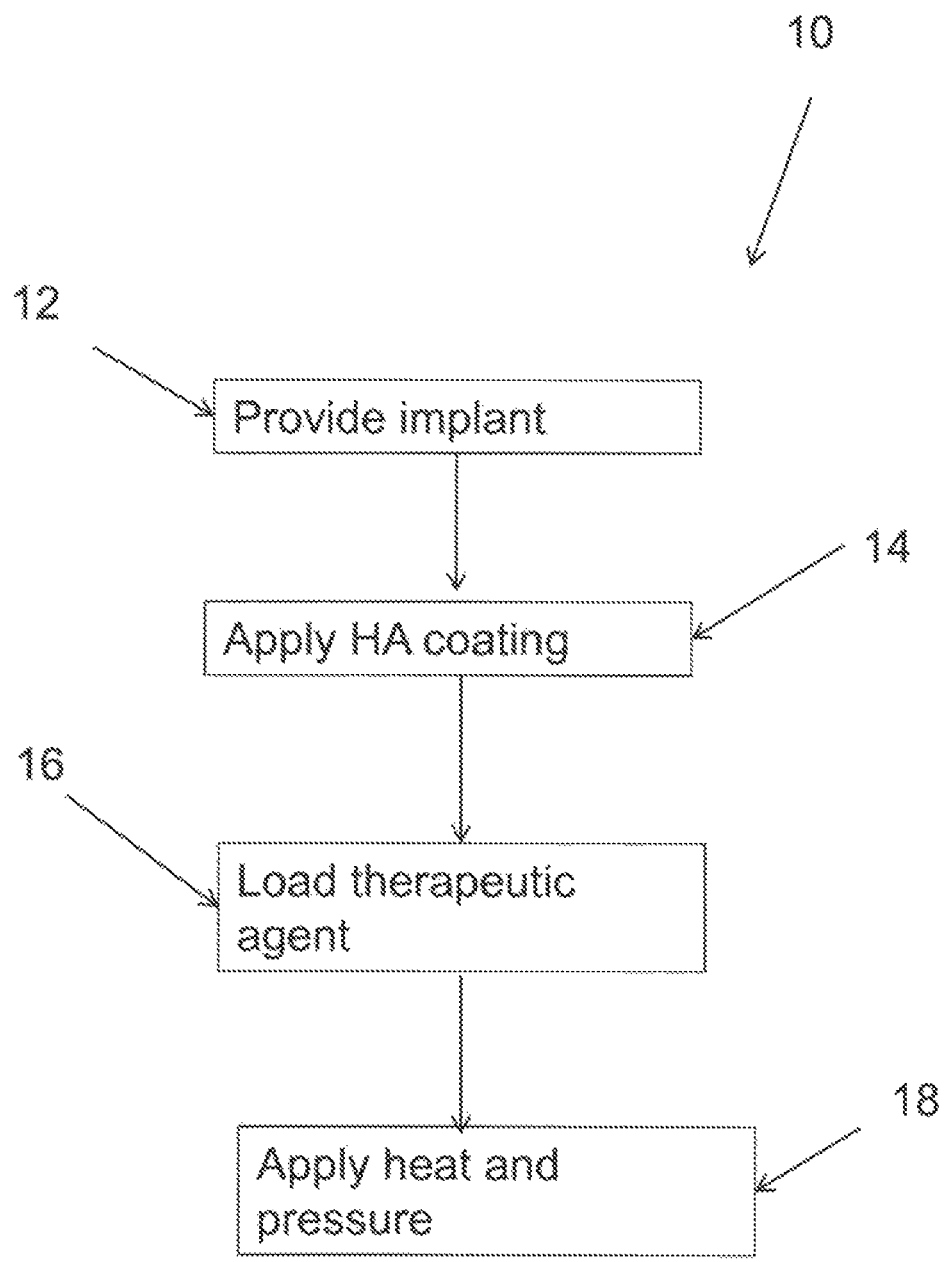
FIG. 1 is a flow diagram illustrating the method of the present disclosure.

Referring to FIG. 1, a process 10 for adsorptive therapeutic agent loading of HA coated implant surfaces for improved drug delivery at the implant site is described. In a first step 12, an implant or medical device is provided. In step 14, the implant is immersed in a simulated body fluid, such as a phosphate buffer saline (PBS) solution. The solution is prepared with various ion concentrations to mimic the chemical composition of human body fluids, such as blood plasma. The implant is soaked in the PBS solution and the HA coating is grown biomimetically.

Prior to applying the HA coating, a surface of the implant was coated with for example, a crystalline $TiO_2$ coating through, for example, cathodic arc evaporation. It should be appreciated that other methods can be used to deposit a volume of the coating. The surface metal coating can be selected from the group of $TiO_2$, $TiO$, $TiCrO_2$, $Ti_2O_3$, $Ti_3O_5$, $SiO_2$, $MgO_2$, $AlO_2$, and $CrO_2$. Because the implant has a base metal of Ti and SSt alloys it is beneficial to provide a bioactive underlying surface so as to nucleate the HA crystals on the metal base. As will be described further herein, the biomimetic coating is applied on the implant base in a thickness of about 1 to about 10 μm.

In steps 16 and 18, the HA coated implants were loaded with a therapeutic agent. The HA coated implants were placed in a solution of dissolved therapeutic agent with a specific concentration thereof. A pressure of about 2-10 bar was applied and the solution and implant were heated to a temperature of about 60° C. to about 1000° C. The resulting penetration depth of the therapeutic agent into the coating is about 0.5 μm to about 8 μm.

Co-precipitation of HA and therapeutic agent can be obtained when the chemical structure, i.e., carboxyl groups in antibiotics, interact with the calcium ions in the HA, or when ions from both the PBS and therapeutic agent simultaneously are incorporated by co-precipitation. The PBS solution can contain calcium and phosphate ions. The ions can also be selected from the group of F, Sr, Si and Mg.

This use of ions or ion doping during biomimetic growth can be used to affect the surface area and surface charge of the HA coating. The coating thickness, porosity and morphology can be varied to achieve differently designed drug delivery profiles, such as different release times with initial burst effect, controlled long term release and/or cycled release. The doped coatings have enhanced affinity to the drugs during loading.

Experiments were conducted using the antibiotic Tobramycin as the therapeutic agent. Tobramycin was incorporated into biomimetically deposited HA—and plasma-sprayed HA coatings on stainless steel fixation pins and the loading and release properties of the antibiotic to the structural coating properties and loading conditions were correlated. Tobramycin was selected due to its broad spectrum against most Gram-negative bacteria and its ability to restrain growth of *Staphylococcus aureus*, which is often connected to post-surgical infections. See Nijhof M. W. et al., "Prophylaxis of Implant-Related Staphylococcal Infections Using Tobramycin-Containing Bone Cement" *J Biomed Mater Res* 52 754-761 (2000). However, it should be appreciated that other antibiotic/drugs/therapeutic agents can be used depending upon the desired effect.

Cathodic arc deposition was used to coat the stainless steel fixation pins with a bioactive, anatase phase dominated $TiO_2$ coating and the HA coating was grown biomimetically on these $TiO_2$ surfaces. As fully described below, the loading and release properties were evaluated by studying the subsequent release of Tobramycin using high pressure liquid chromatography and correlated to the differences in HA coating microstructure and the physical conditions under loading.

Stainless Steel fixation pins (Ø4 mm, 90 mm×30 mm, REF 5023-3-090, LOT W11825) from Stryker Trauma AG (Selzach, Switzerland) were used for coating deposition and plasma sprayed HA coated fixation pins (Ø4 mm, 90 mm×30 mm, REF 5013-3-090S, LOT U24265) also from Stryker Trauma AG served as reference samples. Standard stainless steel plates (20 mm×20 mm×1 mm) of medical grade AISI type 316L served as substrates for X-ray diffraction (XRD) measurements and Glow discharge optical emission spectroscopy investigations.

The pins were coated with a crystalline $TiO_2$ coating through cathodic arc evaporation during a deposition time of 20 minutes, as described previously. XRD measurements on the $TiO_2$ films were performed using a Siemens D5000 diffractometer operating with 1° grazing incidence angle in parallel beam geometry using CuKα radiation (wavelength λ of 1.540598 Å). A step size of 0.1° and a scan step time of 4 s were used for the scans recorded between 20° and 60° 2θ.

A HA coating was biomimetically precipitated on the $TiO_2$ coated pins using Dulbecco's Phosphate Buffered Saline (PBS) as ion source. Following the cathodic arc deposition of the crystalline $TiO_2$, the fixation pins were ultrasonically cleaned in isopropanol and de-ionized water (5 min in each) and subsequently placed in plastic tubes containing 50 ml of PBS. The tubes were kept at 37° C. for 6 days, carefully rinsed in deionized water and left to dry in air.

The biometically precipitated HA (HA-B) coatings as well as the plasma sprayed HA (HA-P) coated pins were examined using a Zeiss Supra 40 Scanning Electron Microscope (SEM) and XRD using the set-up described above, but with a 2θ between 23° and 34°. SEM images of the HA cross sections obtained by ion milling (E-3500, Hitachi) were recorded to evaluate the thicknesses and structures of the deposited HA coatings on the pins. The coating topography was studied by white light interferometer (Wyko NT1100, Veeco) and the surface roughness of the coatings was obtained from the Profiling Software Vision (Veeco).

For antibiotic incorporation into the HA-coatings, Tobramycin (Fargon GmbH & Co. KG, Barsbüttel, Germany) was dissolved in water of double distilled quality. Five different sample types, designated as Load-RT, Load-C, Load-P, Load-HT and Load-PHT, were prepared by varying the loading time, drug concentration, pressure and temperature as detailed in Table 1 below. All samples in the Load-series were made in triplicates for both HA-coating types under study.

TABLE 1

Tobramycin loading parameters for both HA-B and HA-P coatings

| Samples | Temperature [° C.] | Tobramycin concentration [mg/ml] | Loading time [min] | Pressure [bar] |
| --- | --- | --- | --- | --- |
| Load-RT | RT | 40 | 5; 15; 60 | 1 |
| Load-C | RT | 4; 20; 40 | 5 | 1 |
| Load-P | RT | 20 | 5 | 6 |
| Load-HT | 90 | 20 | 5 | 1 |
| Load-PHT | 90 | 20 | 5 | 6 |

To produce samples in the Load-RT, Load-C, and Load-HT series, the HA coated pins were placed in round bottom test tubes (130×14 mm×1 mm) containing 5 ml of Tobramycin stock solution at the concentrations specified in Table I. During the Load-HT drug loading procedure, the test tubes were kept in a heated water quench (Heraeus) while the Load-RT and Load-C samples were produced at room temperature. The Load-P and Load-PHT samples were prepared by placing the HA-coated pins and 30 ml of stock solution containing 20 mg/ml Tobramycin in a stainless steel tube under an applied pressure of 6 bar. The high temperature of 90° C. prevailing during loading of Load-PHT was ensured by preheating the steel tube to 90° C. prior to the loading procedure. The loaded samples from all series were placed for drying in an oven at 37° C. for 24 hours.

For the release studies, the dried samples were placed in round bottom test tubes containing 5 ml of PBS at 37° C. The amount of Tobramycin released from the samples was measured at different time points (typically at 5, 15, 30, and 60 min as well as 4 h, 2, 5, and 8 days) to evaluate both initial and long term slow release properties. Upon completion of the first releasing time point, the pin was transferred to the next test tube containing 5 ml of fresh PBS at 37° C. This cumulative release testing was carried out until no Tobramycin could be measured.

The durability of the HA coatings was investigated with SEM after drug loading and also after drug release. After the last time point measured for the release in PBS, the HA coatings were dissolved by lowering the pH of the PBS to 2 through addition of hydrochloric acid in order to measure the amount of remaining drug present in the coating.

The penetration depth of the antibiotics into the different HA-B sample types was evaluated by Glow discharge optical emission spectroscopy (GDOES, GDA750-HP Spectruma Analytik GmbH, Germany). Quantitative profiles of Tobramycin characteristic elements nitrogen (N) and carbon (C) were obtained by measuring the chemical composition of drug-loaded HA-B samples from the sample surfaces towards the substrate.

High performance liquid chromatography (HPLC) was used to quantify the released drug content as well as the release kinetics. The measurements were performed and modified according to the British Pharmacopoeia "HPLC Detection of Gentamicin Sulphate" Volume I 695-697 (1999) and Fabre H. et al., "Determination of Aminoglycosides in Pharmaceutical Formulations—High-Performance Liquid Chromotography" *J Pharmaceut Biomed* 17 1711-1718 (1989) using pre-column derivatization of the aminoglycoside antibiotic. A 100 ml derivatization reagent was produced by dissolving 2.47 g boric acid R (Carl Roth GmbH) in 75 ml water followed by adjusting the pH to 10.4 by using potassium hydroxide (450 g/l, Sigma-Aldrich). This mixture was diluted with water to 100 ml. 1 g orthophthalaldehyde R (Sigma-Aldrich) was dissolved in 5 ml methanol. This solution was mixed with 95 ml boric acid solution and 2 ml of mercaptoacetic acid from Merck KGaA (Darmstadt, Germany). This derivatization reagent was adjusted to pH 10.4 by adding potassium hydroxide (450 g/l) and stored for a maximum of 7 days, light protected at 2-8° C.

Pre-column derivatization was performed by mixing 1 ml sample solution containing Tobramycin with 1.1 ml methanol and 0.4 ml derivatization reagent. This solution was mixed on a magnetic stirrer at 1400 rpm for 10 minutes. A volume of 100 μl was injected.

The mobile phase consisted of 5.5 g sodium heptanesulphonate (Sigma-Aldrich) solved in a mixture of 50 ml glacial acetic acid, 700 ml methanol and 250 ml double distilled quality water. A flow rate of 1.0 ml/min and a wavelength of 330 nm were carried out using a Hypersil ODS column (3 μm 100×4.6 mm; VDS Optilab Chromatographie Technik GmbH, Montabaur, Germany) as stationary phase at room temperature, a high precision pump (Waters 600E Multisolvent Delivery System), an autosampler (Waters Inline Degasser AF and a Waters 717 plus autosampler), and a Waters UV detector (Waters 996 Photodiode array detector). Data analysis was performed using the Waters Empower 1154 software.

Figure 2:
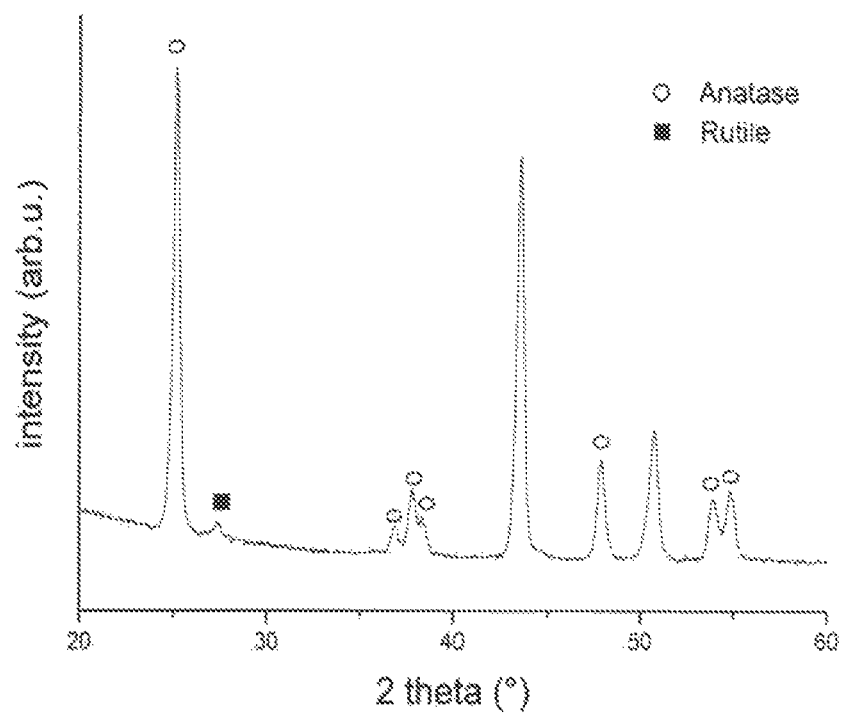
FIG. 2 is an XRD spectrum of the $TiO_2$ coating on a stainless steel substrate.

FIG. 2 illustrates the XRD spectrum of the $TiO_2$ coating on a stainless steel substrate. As shown, the microstructure of the $TiO_2$ coatings is dominated by the anatase phase with minor amounts of rutile present in the structure.

Figures 3A, 3B, 3C, 3D:
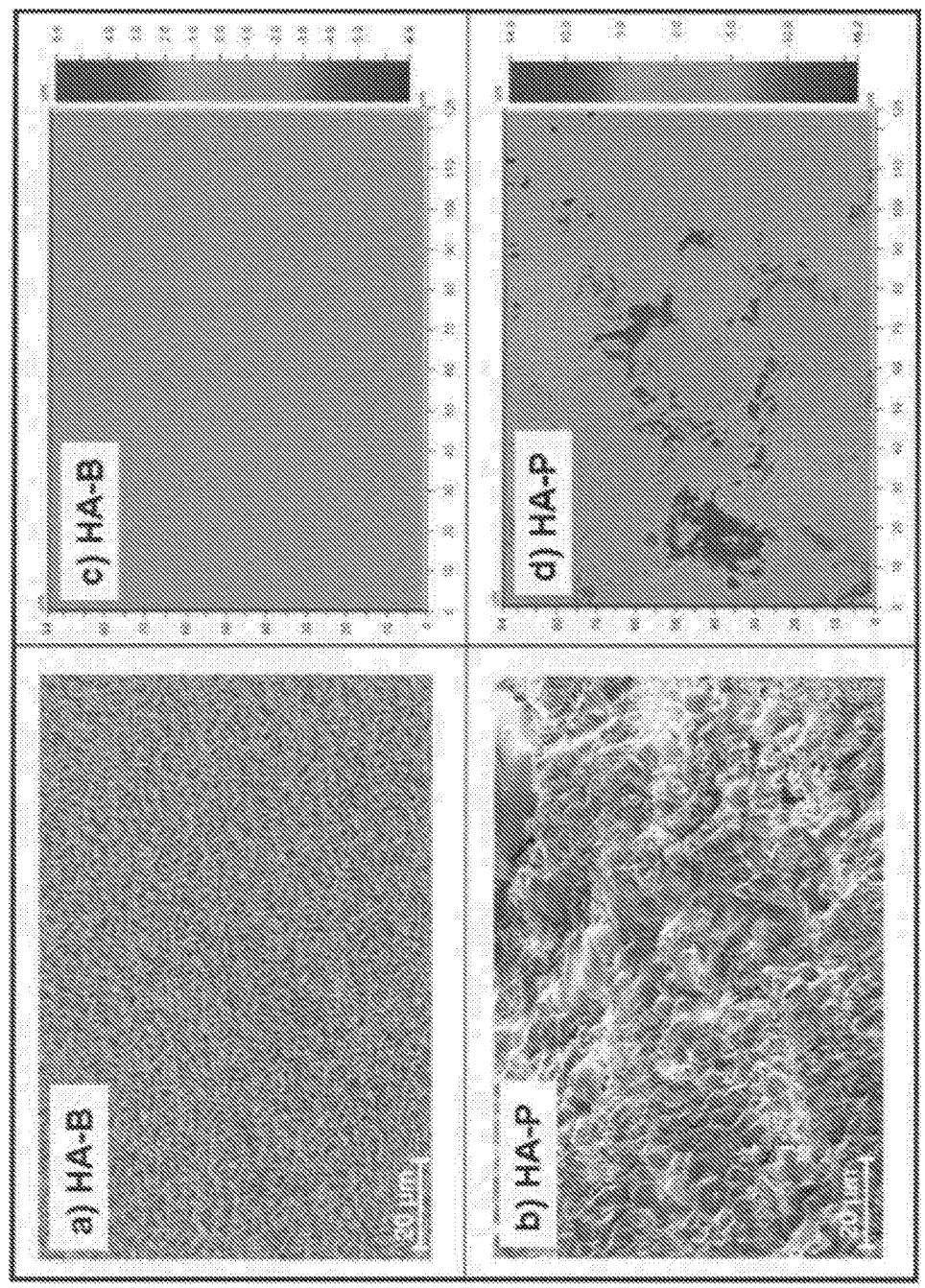
FIGS. 3(a) and 3(d) are SEM images and surface topography maps of the surface of biomimetically deposited HA-B samples FIGS. 3(a) and 3(c) and plasma sprayed HA-P samples FIGS. 3(b) and 3(d).
Figure 4:
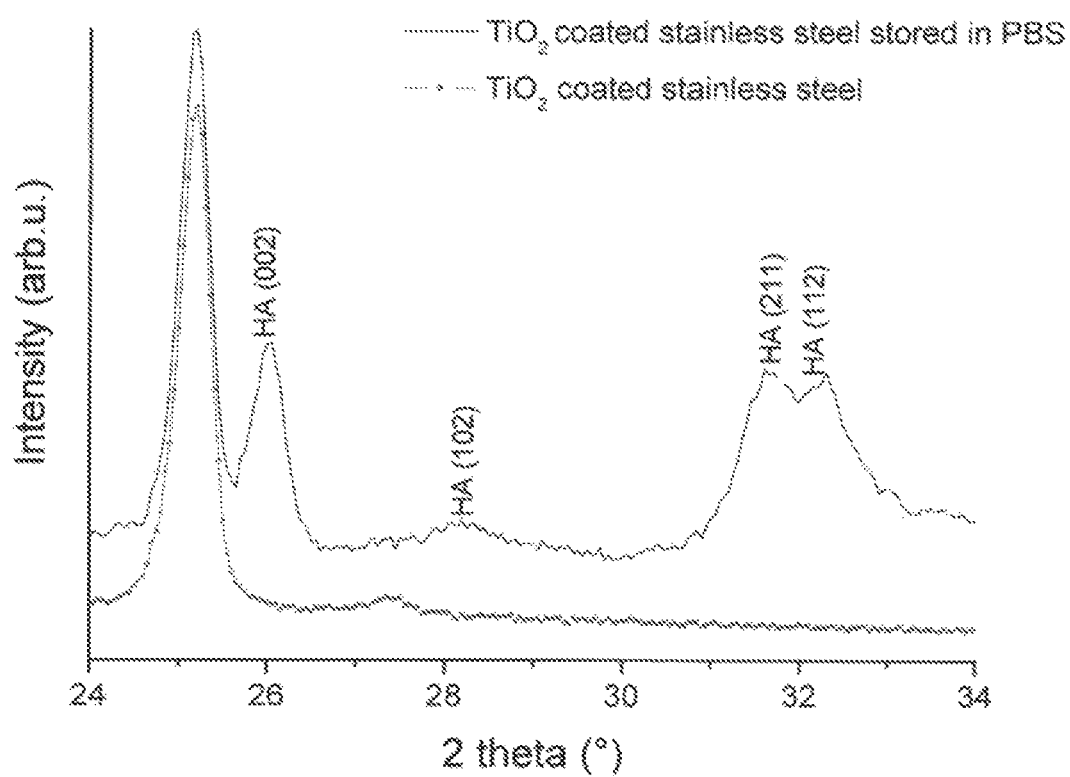
FIG. 4 is an XRD spectra of $TiO_2$ and $TiO_2$ coated stainless steel plates stored in PBS. Diffraction peaks of crystalline HA are indicated.
Figures 5A, 5B:
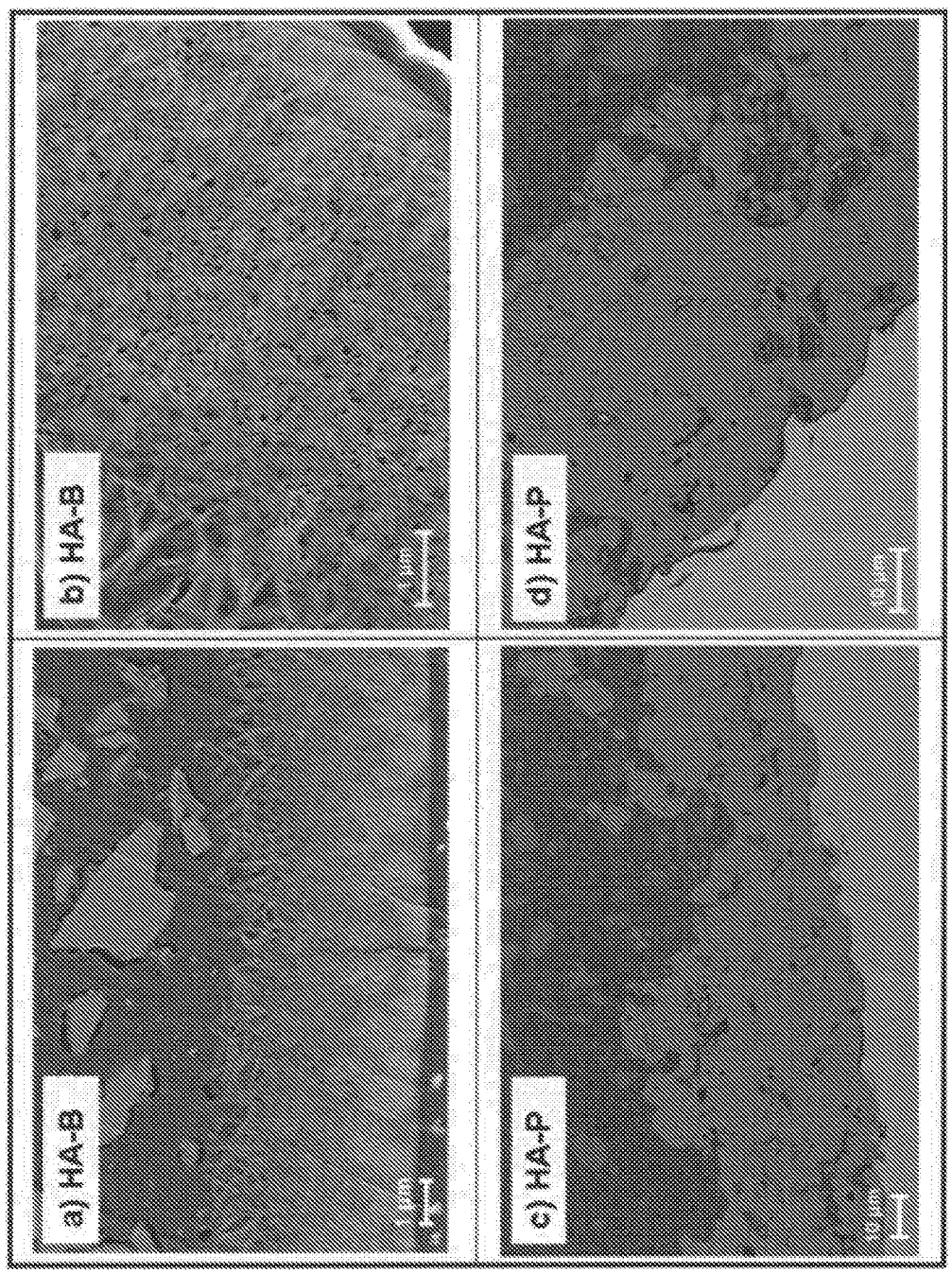

As visualized by the SEM images in FIGS. 3a and 3b, the HA deposition process had a strong impact on the HA-coating morphology. Immersion of the $TiO_2$ coated pins in PBS resulted in precipitation of a nanoporous, continuous HA-B coating with needle-like HA crystals, FIG. 3a, whereas the plasma deposited HA-P had a rather rough morphology, consisting of droplets and variation in substrate coverage, FIG. 3b. The surface topography maps, FIGS. 3c and 3d, confirm the much rougher surface of the plasma deposited HA coating seen in the SEM images. The surface roughness of the coatings was characterized by a profile roughness, $R_a$, of approximately 2.5-3 μm and approximately 0.5-1.0 μm for the HA-P and the HA-B coatings, respectively. XRD measurements of HA-B coated plates confirmed that the coating indeed consisted of crystalline HA, see FIG. 4. FIG. 4 shows the XRD spectra of $TiO_2$ and $TiO_2$ coated stainless steel plates stored in PBS. Diffraction peaks of crystalline HA are indicated in the figure.

SEM images of the coating cross-sections are displayed in FIG. 5(a)-5(d). The HA-B coating, FIGS. 5(a) and 5(b), displays a dense, nanoporous, structure near the $TiO_2$ interface and a higher degree of porosity with a flake-like topography near the outer surface. The thickness of HA-B deposited coatings varied between approximately 4 and 8 μm. A higher coating thickness is noted in the thread valleys of the pins then at the thread tops for the HA-B coatings. In comparison, the HA-P coatings have an average thickness between ~20 and 40 μm. Cracks and micropores can be observed in the cross section SEM images of these samples, FIGS. 5(c) and 5(d).

After the last time point measured for the Tobramycin release in PBS for all coatings under study no drug was detected in the coating as confirmed by HPLC analysis on the solution containing the pH2 dissolved coatings. Thus, the release data presented in FIGS. 6 and 7 covers the complete release of the entire amount of drug loaded into the coatings.

Figure 6A:
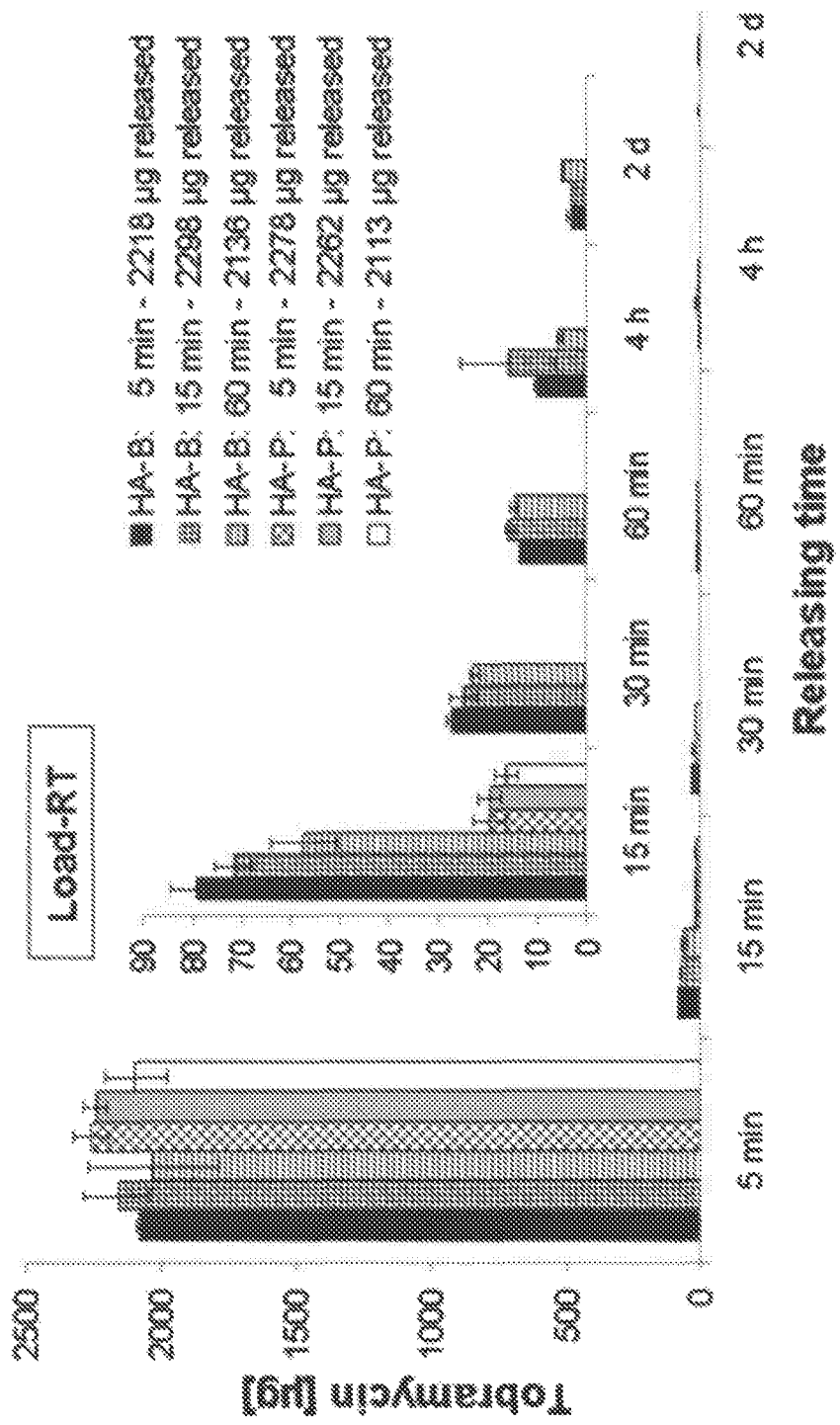
FIGS. 6(a)-(b) are graphs of non-cumulative amount of Tobramycin released in 37° C. PBS from HA-P and HA-B coated pins of the (a) Load-RT series after being loaded in a solution containing 40 mg/ml of the antibiotics during the displayed loading times and from the (b) Load-C series after being loaded during 5 minutes in solutions with the displayed concentrations of antibiotics.

During the entire release period the amount of Tobramycin released from all sample types was above the MIC for *Staphylococcus aureus* D'Arrigo M. et al., "Synergism and Postantibiotic Effect of Tobramycin and *Melaleuca Alternifolia* (teatree) Oil Against *Staphylococcus Aureus* and *Escherichia Coli*" 17 317-322 (2010). A non-cumulative amount of Tobramycin was released in 37° C. PBS from HA-P and HA-B coated pins. FIG. 6(a) shows the Tobramycin release in PBS from the Load-RT samples after being loaded in a solution containing 40 mg/ml of the antibiotics during the displayed loading times. The total amount of drug released does not show any clear dependence on the drug loading time. An initial, rapid, burst-like release is observed for both types of HA coatings during the first 5 minutes of release. This burst release results in a complete release of the antibiotic content of the HA-P samples after only 15 minutes while a continuous, and steadily decreasing, release of Tobramycin is observed from the HA-B coatings during 2 days.

Figure 6B:
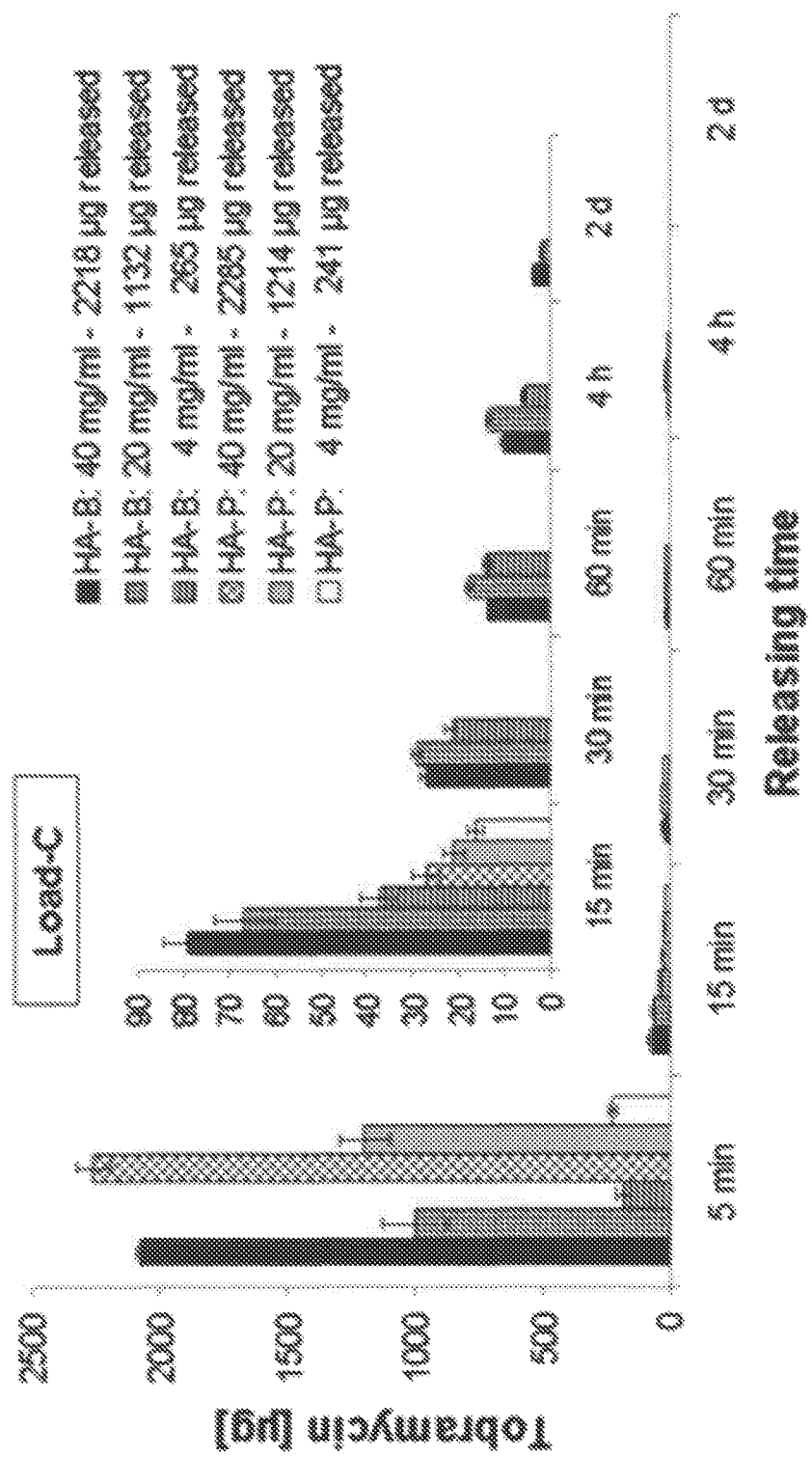

The impact of different drug loading concentrations on the release kinetics is presented in FIG. 6(b), which shows the Load-C series after being loaded during five minutes in solutions with the displayed concentrations of antibiotics. Error bars denote the standard deviation of three measurements. The average total of Tobramycin released from each coating type are also displayed. Just as for the Load-RT samples (of which the 5 minute loading time samples are identical to the 40 mg/ml concentration Load-C samples), the Load-C samples exhibited an initial burst release, which is followed by a continuous release during 2 days for the HA-B samples and which results in elution of the antibiotic content of the HA-P samples after only 15 minutes.

The amount released during the first 15 minutes increases linearly with increasing drug loading concentration for both the HA-B and the HA-P coatings. No clear correlation between the antibiotic concentration used during loading and the amount released after the initial burst during the sustained release period from the HA-B samples is seen. Based on these results a drug loading time of 5 minutes and a drug concentration of 20 mg/ml for the preparation of Load-P, Load HT, and Load-PHT were used. For the evaluation of these samples, the Load-C samples prepared using the same drug loading concentration was used as a reference and hereafter denoted as Ref-RT.

Figures 7A, 7B, 7C:
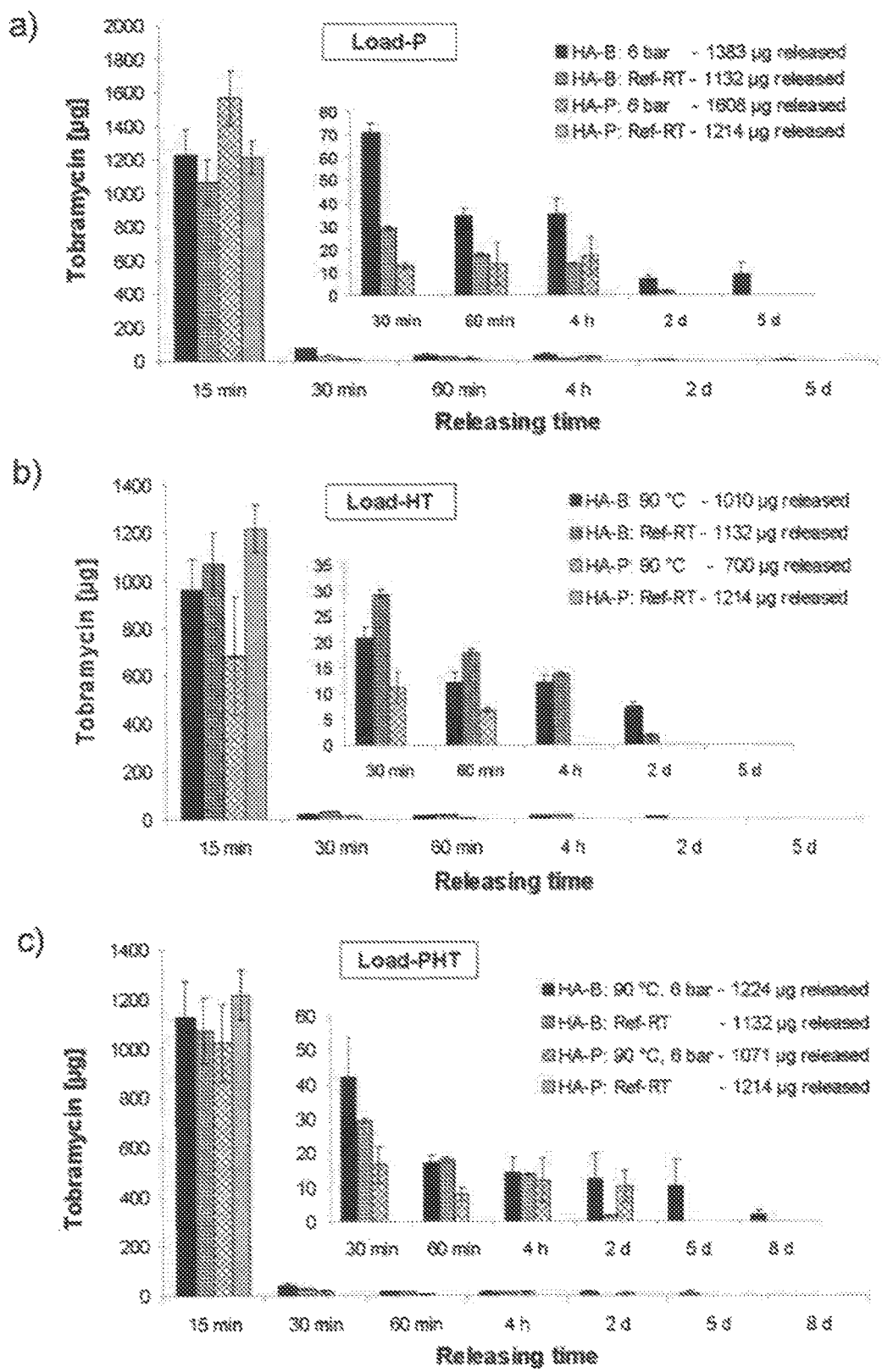
FIGS. 7(a)-(c) are graphs of non-cumulative amount of Tobramycin released in 37° C. PBS from HA-P and HA-B coated pins from the (a) Load-C, (b) Load-HT and (c) Load-PHT series after being loaded for 5 minutes in a solution containing 20 mg/ml of the antibiotics under a) a pressure of 6 bar, b) at 90° C. and c) at 90° C. and 6 bar.

The effect of pressure during drug loading on the release process is displayed in FIG. 7(a), showing the amount of released Tobramycin from the Load-P samples with the corresponding values from the Ref-RT samples. FIGS. 7(a)-(c) show non-cumulative amount of Tobramycin released in 37° C. PBS from HA-P and HA-B coated pins from the a) Load-C, b) Load-HT and c) Load-PHT series after being loaded for 5 minutes in a solution containing 20 mg/ml of the antibiotics under a) a pressure of 6 bar, b) at 90° C. and c) at 90° C. and 6 bar. Release results from reference samples loaded during 5 minutes in similar solutions at atmospheric pressures and room temperature are incorporated. Error bars denote the standard deviation of 3 measurements. The average total amounts of Tobramycin released from each coating type are also displayed. The higher pressure during drug loading contributes to an increase in the total amount of drug loaded into and released from both coating types as well as a prolonged sustained release period. Instead of emptying the entire antibiotic content in only 15 minutes, the HA-P coatings of Load-P samples had a sustained release for 4 hours. Similarly, the release period from the HA-B coatings was extended from 2 days to 5 days.

Figure 8A:
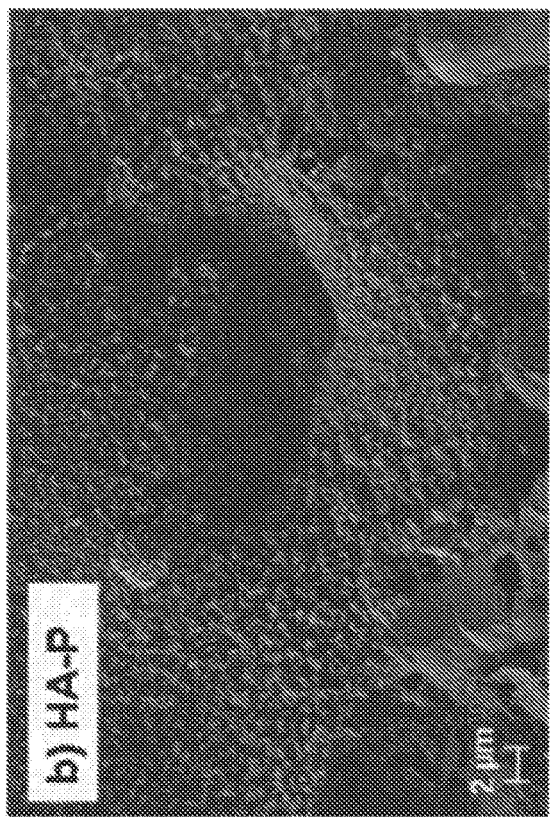
FIGS. 8(a)-(b) are SEM images of HA-B (a) HA-P (b) coatings from the Load-P series after 5 days of Tobramycin release in PBS.
Figure 8B:
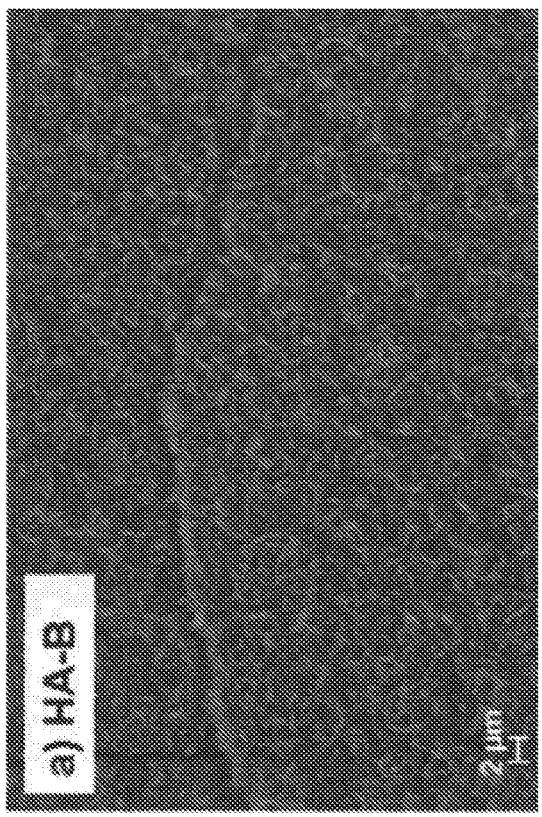

SEM images of HA-B (a) HA-P (b) coatings from the Load-P series after 5 days of Tobramycin release in PBS are shown in FIGS. 8(a)-(b). No indications of dissolution or alteration of the HA-B coatings in the Load-P sample series could be observed after the release studies, see FIG. 8(a). On the other hand, flake-like HA crystals were found on the HA-P surfaces after 5 days of release in PBS, FIG. 8(b). Cracks in the coating structure are observed for both coating types and can be ascribed to the loading method or the drying process.

The influence of elevated temperature during drug loading is shown in FIG. 7(b), which displays the amount of released Tobramycin from the Load-HT samples with the corresponding values from the Ref-RT samples. The total amount of Tobramycin incorporated into both HA coating structures at 90° C. is found to be lower than the corresponding values incorporated at room temperature. An increased sustained release time of 60 min could, however, be obtained for HA-P coated pins while HA-B coatings exhibited an increase in released amount of drug after 2 days.

FIG. 7(c) shows the combinatorial impact of elevated temperature and pressure, used for the Load-PHT samples, during drug loading. A substantial improvement in the sustained release properties of both the HA-B and HA-P coatings are observed. The total release time period is increased to 2 days and 8 days, respectively, for the HA-P and HA-B samples in the Load-PHT series as compared to only 15 minutes and 2 days for the corresponding reference samples. The total amount of drug incorporated into the HA-B samples is slightly increased (~8%) while the corresponding amount for the HA-P samples is decreased (~12%).

Figures 9A, 9B:
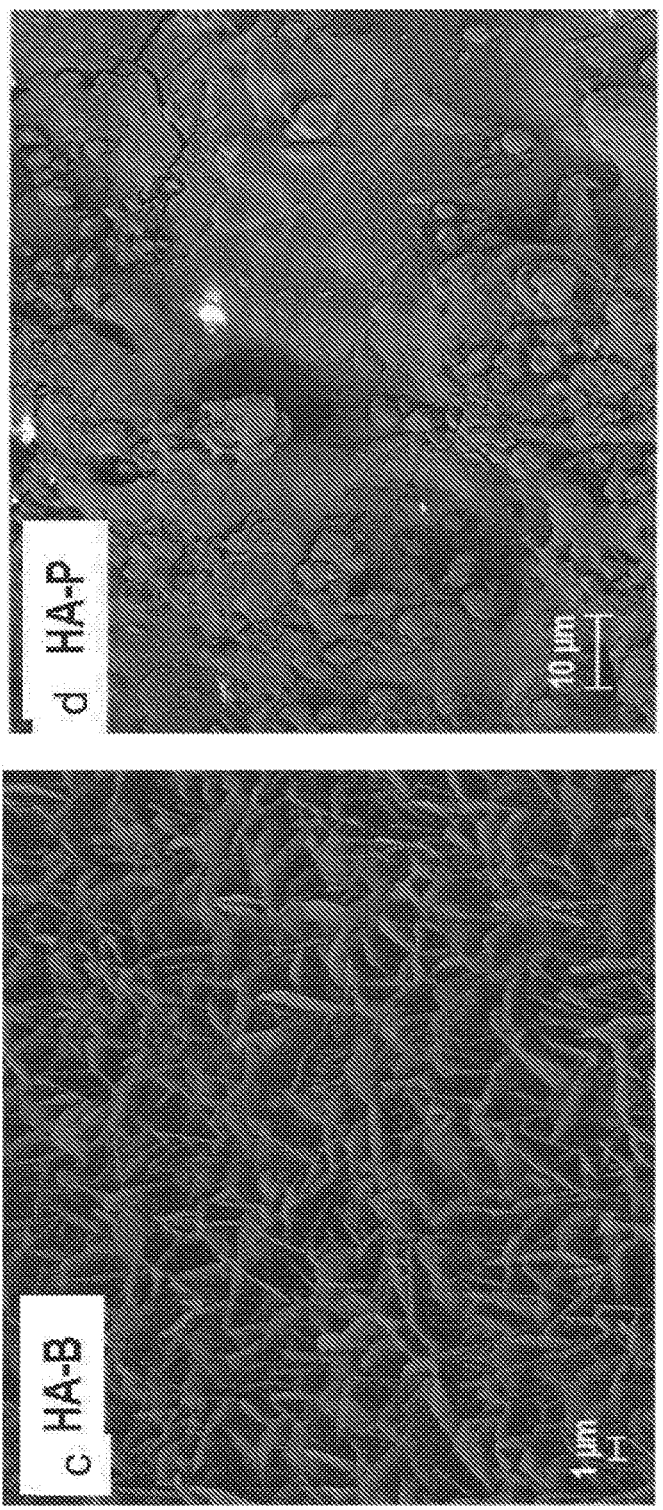
FIGS. 9(a)-(b) are SEM images of HA-B (a) and HA-P (b) coatings loaded with Tobramycin under a pressure of 6 bar (Load-P).

FIGS. 9(a) and 9(b) are SEM images of HA-B (a) and HA-P (b) coatings loaded with Tobramycin under a pressure of 6 bar (Load-P). The incorporation of antibiotics into the HA coatings did not cause any detectable morphological changes, as obvious from the comparison with the coating topographies in the as-deposited state shown in FIG. 3(a)-(b).

SEM images of HA-B (a) and HA-P (b) coatings loaded with Tobramycin under a pressure of 6 bar (Load-P). The incorporation of antibiotics into the HA coatings did not cause any detectable morphological changes, as obvious from the comparison with the coating topographies in the as-deposited state, see FIG. 3.

Figures 10A, 10B:
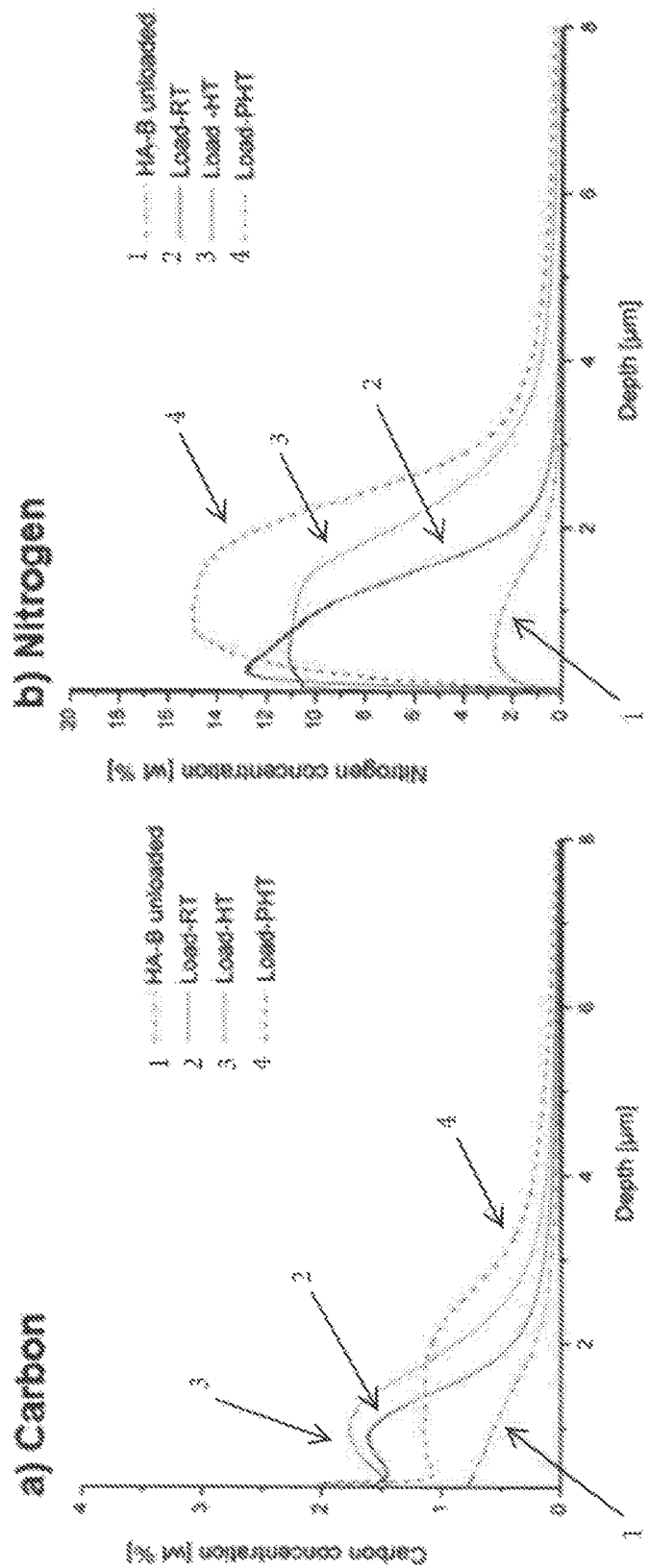
FIGS. 10(a)-(b) are depth profiles of carbon (a) and nitrogen (b) of a HA-B sample loaded with 20 mg/ml Tobramycin under the displayed loading series.

FIGS. 10(a) and (b) present the C- and N-depth profiles of loaded HA-B samples loaded with 20 mg/ml of Tobramycin under the displayed loading series obtained from GDOES measurements. The corresponding profiles of an unloaded sample are incorporated as reference. The drug loading parameters are observed to strongly influence the penetration depth of the antibiotic into the porous HA-B coating structure. The C- and N-profiles of Load-RT samples show that Tobramycin is present close to the sample surface with a peak concentration at a coating depth of about 1 µm. An evaluated temperature of 90° C. during loading contributes to a slightly increased penetration depth of the drug as evident from the broadening of both C- and N-profiles for the Load-HT samples. Drug incorporation under increased temperature and pressure results in the highest N-concentration of all samples and a drug penetration depth of approximately of about 3-4 µm. Thus, the conditions under which Load-PHT samples are made allow the drug to be incorporated into the denser part of the HA-B coating, see FIG. 5(a).

In summary, Tobramycin loading and release properties of biomimetic and plasma sprayed HA coated fixation pins with respect to HA coating structure and drug loading parameters was investigated. The results show that coating porosity and selected physical conditions for loading, such as temperature and pressure, are important parameters for tailoring of the release profile. An initial burst like release was observed from both biomimetically deposited HA-B samples and plasma sprayed HA-P samples, FIGS. 6(a)-(b). No release following this initial burst could be observed for HA-P samples loaded at room temperature, while a sustained release period during 2 days was achieved from the corresponding HA-B samples. It may be that the nanoporous structure of the HA-B samples, FIGS. 5(a) and (b), facilitated drug loading into the interior of such coatings, thus, enabling a longer drug release period, while the denser structure of HA-P samples, FIGS. 5(c) and (d), most likely restricts the drug penetration depth of these samples making only superficial drug adsorption possible. The latter is in agreement with results obtained in previous studies. Whilst in contrast to what has been observed in earlier studies, no clear correlation between soaking time and total drug loading capacity for the room temperature loaded samples could be found.

A linear correlation was observed between the drug loading concentration and the amount of Tobramycin released during the initial burst release period from both sample types under study, FIG. 6(b). This correlation was anticipated since the initial burst, according to the above discussion, is expected to stem from drugs residing in the outmost layer of the coating, and the amount present in this layer to correlate to the concentration in the loading solution.

No clear correlation was found between the antibiotic concentration used during loading and the amount released during the sustained release period from the HA-B samples. The lack of correlation may be attributed to the assumption that a concentration restricted amount of Tobramycin was present in the pore structure. As described by Stigter M. et al., "Incorporation of Tobramycin into Biomimetic Hydroxyapatite Coating on Titanium" 23 4143-4153 (2002), the molecular structure of Tobramycin determines the interaction with HA and may, thus, limit the incorporation of the drug into the structure to a maximum value, as indicated for concentrations greater than 20 mg/ml, FIG. 6(b).

The nanoporous structure of the HA-B coatings was further shown to play an important role in influencing the loading capacity and the sustained release profile. Elevated pressure under drug loading contributed to a significantly prolonged sustained release period, as well as to an increased amount of total drug incorporated for HA-B Load-P and Load-PHT samples, FIGS. 7(a) and (c), most likely due to penetration of Tobramycin into profound regions of the coating structure. Such penetration could be confirmed by the C- and N-depth profile of the coatings, see FIGS. 10(a) and (b). The increased pressure during drug loading resulted in a sustained release also for the HA-P samples, FIGS. 7(a) and (c), however the release period was shorter than for the HA-B samples. The observed sustained release from the HA-P Load-P and Load-PHT samples may be explained by Tobramycin solution being able to penetrate into micropores present in the coating structure, see FIGS. 5(c) and (d), under elevated pressure.

Whereas increased pressure contributed to increasing both the amount released during the initial burst period as well as during the sustained release period for both coating types under study, FIG. 7(a), elevated temperatures had a counteracting effect on the initial burst release, FIG. 7(b).

The viscosity of the antibiotic containing loading solution decreases with increased temperature and at the same time the antibiotic diffusion coefficient is expected to increase. Hence, Tobramycin should be able to reach further into the coating structure during 5 min loading at 90° C. than during the same time period at room temperature. This readily explains the results in FIG. 7(b) showing that both Load-HT coatings under study (HA-B and HA-P) release more during the last period of detectable release than the corresponding Ref-RT samples (30 and 60 min time points for HA-P and 2 day time point for HA-B). The fact that the elevated temperature also results in a diminishing amount of drug adsorbed in the surface regions of the coating, as evidenced by the diminished burst release, FIG. 7(b), shows that the temperature of 90° C. is high enough to prevent some of the drug molecules to bind to sites in this surface region. A part of the drug that is hindered from binding is diffusing into the coating, but since the total amount of drug residing in the Load-HT coatings is lower than the corresponding amount for the Ref-RT samples, one can conclude that a significant fraction is diffusing back into the loading solution.

The nitrogen concentration profile of the HA-B Load-HT coating in FIG. 10(b) gives further support to the above described distribution of antibiotics in the coatings. The assumed effect of temperature on drug distribution is further supported by the release profiles observed from the Load-PHT samples, FIG. 7(c). Whereas elevated pressure and temperature both increase the penetration depth of the drug during loading, the parameters counteract each other when it comes to drug incorporation in the surface regions of the coatings. The HA-B coatings show a sustained Tobramycin release for as long as 8 days whereas the release from the HA-P coatings continues for 2 days instead of just 15 minutes (Ref-RT). The surface binding inhibition induced by the elevated temperatures results in a lower total amount of incorporated Tobramycin in the HA-P Load-PHT samples as compared to the corresponding Ref-RT samples. For the HA-B samples, on the other hand, the porous coating structure, FIGS. 5(a) and (b), ensures a dominance of the increased penetration depth effect over the surface binding inhibition effect leading to an increased total amount of drug incorporated in the HA-B Load-PHT samples compared to the corresponding Ref-RT samples.

The observed HA crystal growth on HA-P coatings, FIG. 8(b), confirmed the total release of Tobramycin from these surfaces and the bioactivity of the plasma sprayed surface itself. As has been shown earlier the presence of drugs in the PBS buffer hinders the formation and growth of HA crystals on bioactive surfaces and thus no HA formation is expected with Tobramycin eluting from the HA-P coating.

The presented findings emphasize the advantages of the nanoporous structure of biomimetically deposited HA over the more dense structure of plasma sprayed HA coatings in terms of antibiotics incorporation and subsequent sustained release. HA coating porosity, coating thickness and drug loading conditions are elemental parameters that can be used to optimize and tailor drug loading capabilities and capacity.

A successful incorporation of Tobramycin into plasma sprayed and biomimetically coated fixation pins was achieved using an adsorptive loading procedure. In addition to the initial burst release seen from the much denser plasma sprayed coatings, the highly porous structure of biomimetically deposited HA coatings allowed for a prolonged sustained release that dominated the release process.

A drug release over a period of 8 days, characterized by a Tobramycin concentration in the release medium above the MIC value for *Staphylococcus aureus*, was obtained for HA-B coatings after drug loading for only 5 min at high temperature and pressure. The combination of an initial burst release and a long period of sustained antibiotic delivery from an orthopedic implant surface are expected to be effective both for preventing and combating implant-related bacterial infections.

It has previously been shown that antibiotic loading during 15 minutes with a subsequent slow release for 1 day is possible with biomimetically deposited planar surfaces. However, a method for fast-loading and slow-release from surgical implants ensuring release times of more than a week, as shown in the present disclosure, has not been previously shown. The short loading time of 5 minutes is foreseen to open up possibilities of developing implant kits where the implant and the drug are separated when delivered to the clinics. In this way the issues associated with sterilization of implants containing drugs prior to packaging are avoided. As well, the fast-loading slow-release concept offers an option to quickly add an antibiotic to an implant coating, thus creating a flexible solution for the surgeon.

The results show that a dual loading strategy consisting of a solution temperature of about 90° C. and a pressure of about 6 bar during a loading time of about 5 min release a sufficient amount of Tobramycin to guarantee the inhibition of *Staphylococcus aureus* for up to about 2 days for plasma sprayed HA coatings and for about 8 days for biomimetic coatings.

A drug release of 8 days, characterized by a Tobramycin concentration in the release medium above the MIC value for *Staphylococcus aureus*, was obtained for biomimetic HA coatings after drug loading for only 5 min at a temperature of 90° C. and a pressure of 6 bar. In comparison, plasma sprayed coatings exhibited a maximum release time of only 2 days. Thus, the advantages of the nanoporous structure of biomimetically deposited HA over the more dense structure of plasma sprayed HA coatings in terms of antibiotics incorporation and subsequent sustained release were shown and a valuable outline for the design of implant surfaces aiming for a fast-loading and controlled, local drug administration provided.

Figure 11A:
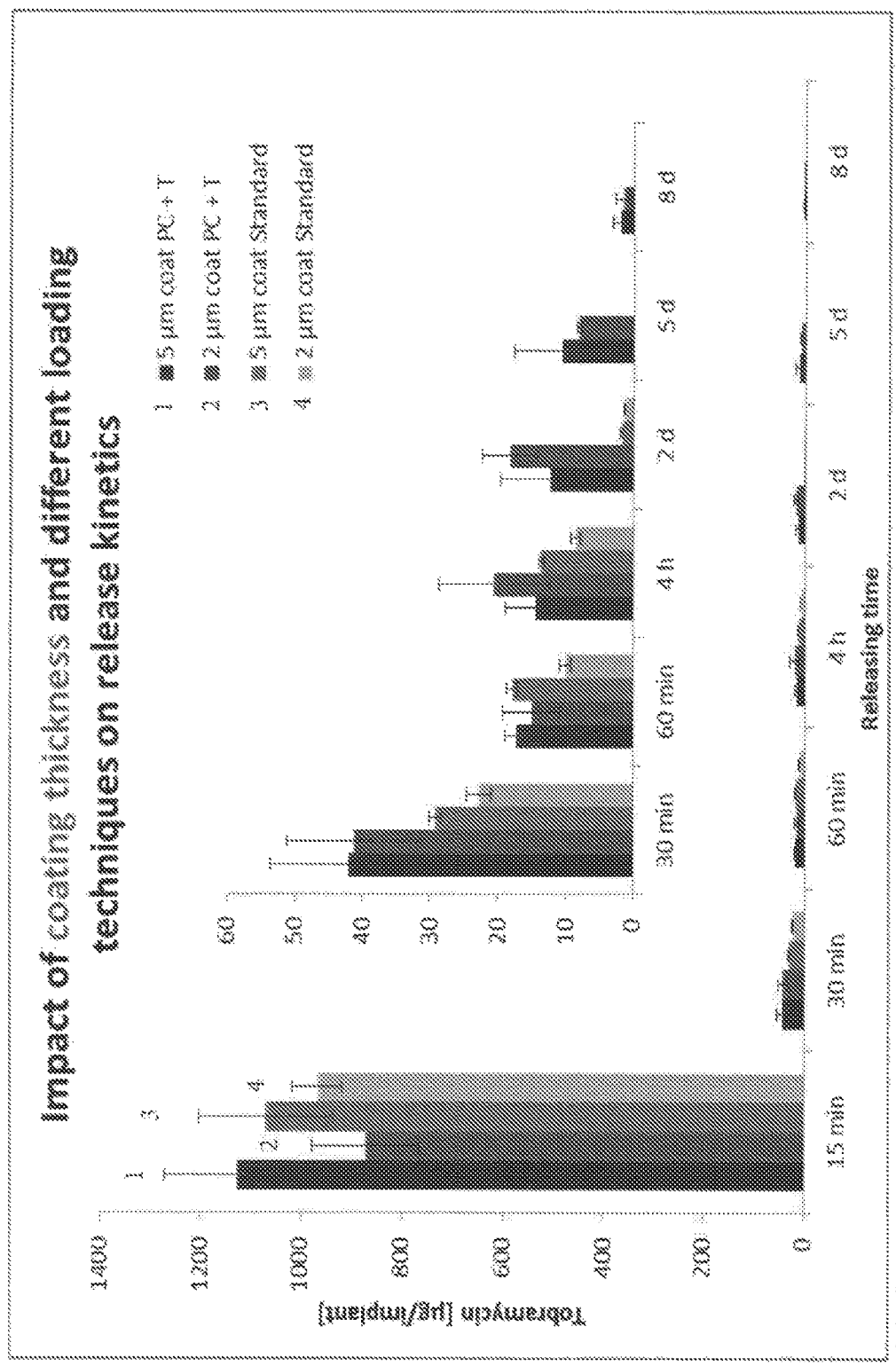
FIGS. 11(a) and 11(b) are graphs of the impact of coating thickness and porosity of different loading techniques on release kinetics.
Figure 11B:
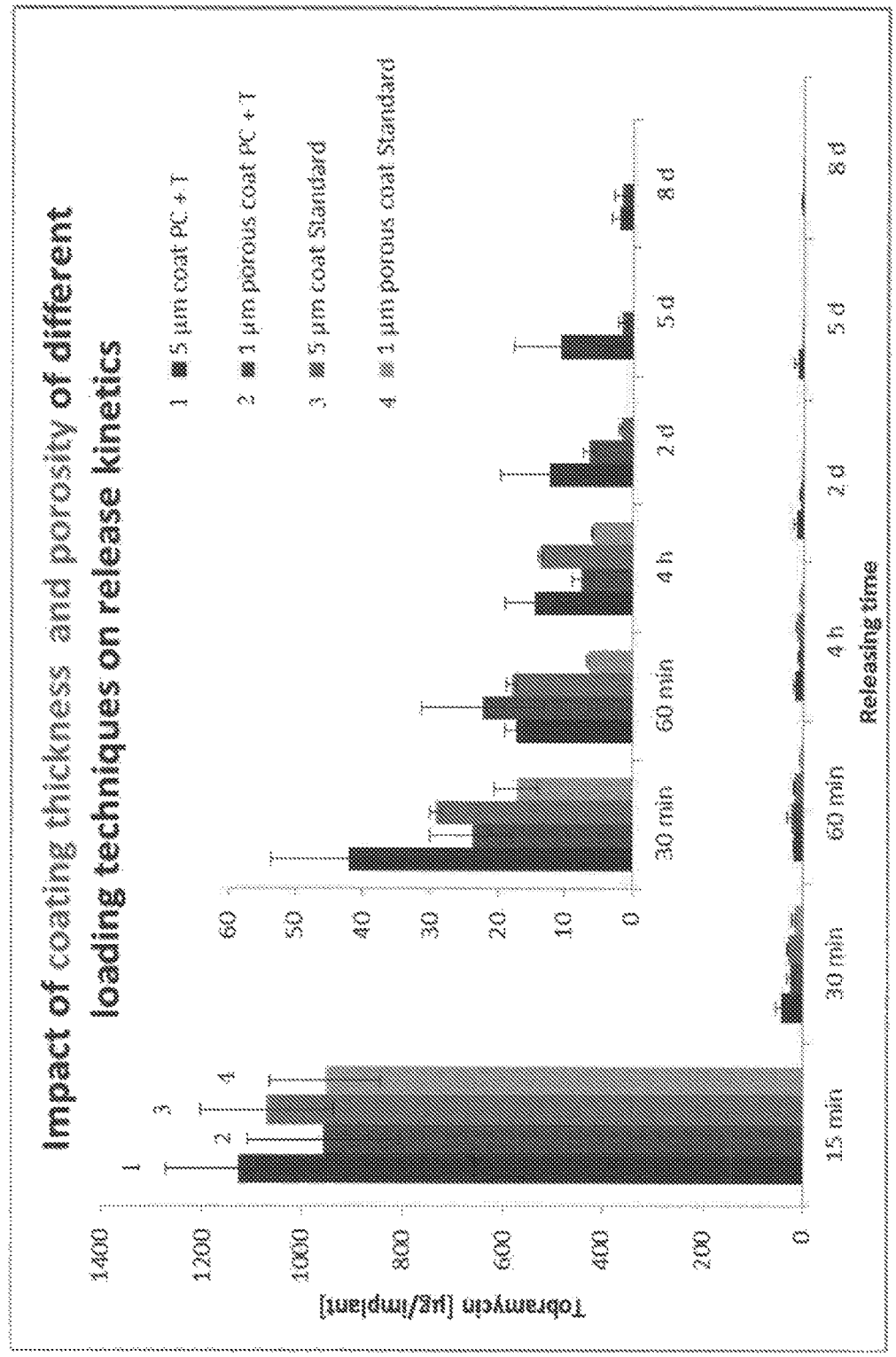

Referring to FIGS. 11(a) and 11(b) the impact of coating thickness on release kinetics was studied. The coatings were made at a PBS temperature of 60° C. and have a different morphology than those at 37° C. With using the 60° C. PBS temperature during deposition the crystal size and coating porosity was impacted. FIG. 11(a) illustrates the impact of coating thicknesses of 2 μm and 5 μm and different loading techniques on release kinetics. FIG. 11(b) illustrates the impact of coating thicknesses of 1 μm and 5 μm and porosity of different loading techniques on release kinetics. As shown, the 5 μm thick coating shows a higher sustained release compared to the 1 and 2 μm thick coatings. The 1 μm thin porous coating showed a sustained release up to four hours with standard loading. With optimized loading (90° C. and 6 bar), the 5 μm coating shows a higher release after four hours, two days and five days. The 1 μm coating also showed a sustained release up to eight days with optimized loading.

Figure 12:
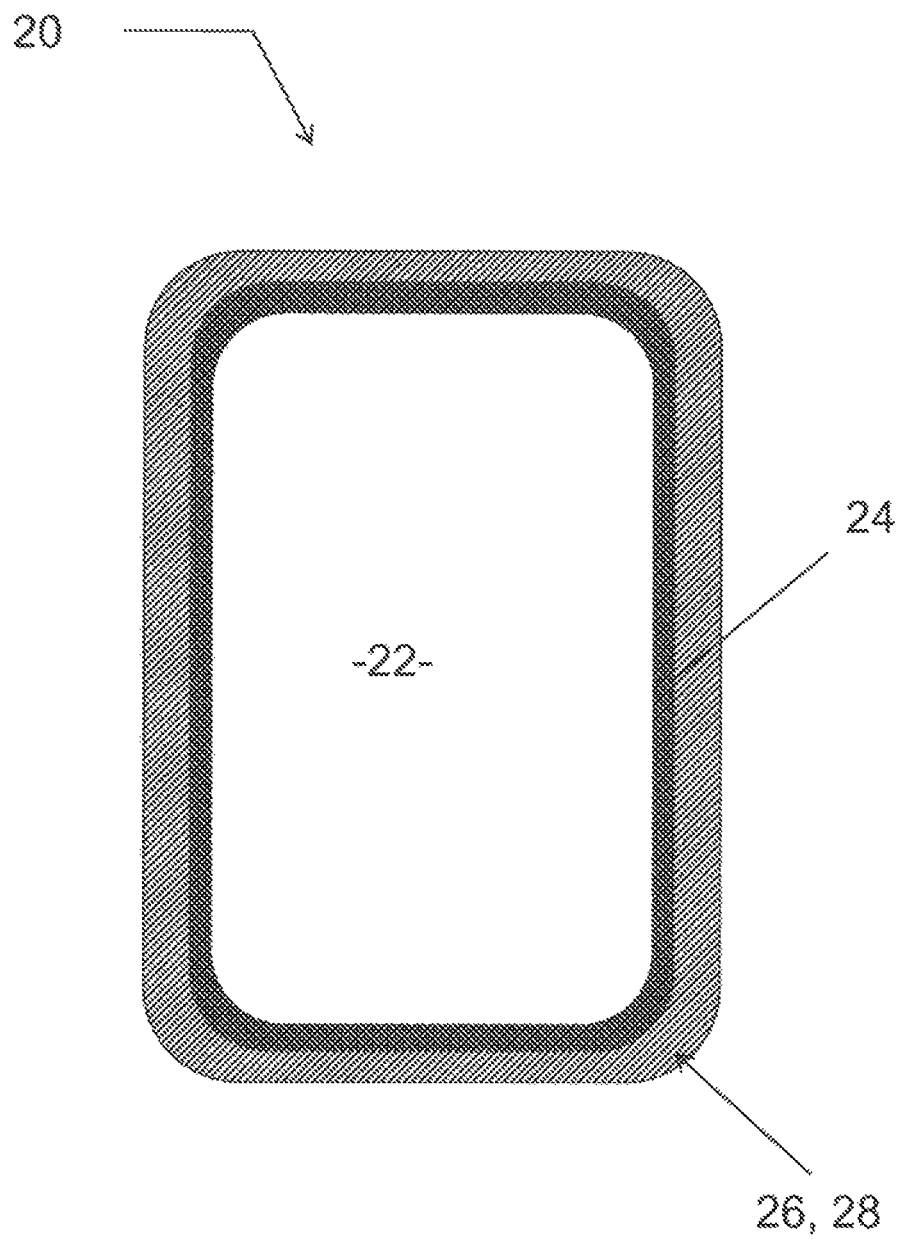
FIG. 12 is a cross-section of an implant made according to the method of the present disclosure.

An implant having sustained therapeutic agent delivery made according to the method of the present disclosure is shown in FIG. 12. As described above, implant 20 can be a device selected from the group of fixation pins, orthopedic devices, dental implants, stents, drug delivery devices, sheets, films, meshes, soft tissue implants, implantable electrodes, implantable sensors, drug delivery pumps, tissue barriers and shunts. Implant 20 includes a base 22 of a metal of Ti and SSt alloys. Base 22 can be a material selected from the group of titanium, titanium alloy, nickel-titanium alloy, tantalum, platinum-iridium alloy, gold, magnesium, stainless steel, chromo-cobalt alloy, ceramics, biocompatible plastics or polymers and combinations thereof.

Base 22 includes a surface coating 24. Surface coating 24 can be selected from the group of $TiO_2$, TiO, $TiCrO_2$, $Ti_2O_3$, $Ti_3O_5$, $SiO_2$, $MgO_2$, $AlO_2$, and $CrO_2$. It should be appreciated that other materials can be used for the base and surface coating thereof. An hydroxyapatite coating 26 is disposed on surface coating 24 of the base. Hydroxyapatite coating 26 can be biometrically grown and has a thickness of about 1 to about 10 μm.

Hydroxyapatite coating 26 is loaded with a therapeutic agent 28. Therapeutic agent 28 is selected from the group of antibiotics, vitamins, chemotherapy drugs, bisphosphonates, strontium-ranelate, PTH, osteoporotic drugs, growth factors, or a combination thereof. As described supra, therapeutic agent 28 is loaded in the coating by heating the hydroxyapatite coated base in a solution of therapeutic agent to a temperature of about 60° C. to about 100° C. and applying pressure of about 4 to about 8 bar to the hydroxyapatite coated base and solution for improved therapeutic agent deposition. Therapeutic agent 28 has a hydroxyapatite coating penetration depth of about 0.5 to about 8 μm.

In summary, the effectiveness of antibiotics-loaded implant coatings is strongly dependent on the drug release profile. If the antibiotics are released at levels below the minimum inhibition concentration (MIC), bacterial resistance may be induced at the release site. An optimum local antibiotic release profile for orthopedic implants should feature a high initial release rate during the first hours after implantation, followed by a sustained release to inhibit the occurrence of latent infection and allow for protective fibrous capsule formation as well as tissue integration.

Although the present disclosure has been described in relation to particular embodiments thereof, many other variations and modifications and other uses will become apparent to those skilled in the art. It is preferred therefore, that the present disclosure be limited not by the specific disclosure herein, but only by the appended claims.

What is claimed is:

1. A method for loading a hydroxyapatite coated implant with a therapeutic agent, comprising the steps of:
   providing an implant;
   applying a hydroxyapatite coating on a surface of the implant;
   contacting the hydroxyapatite coated implant with a solution including the therapeutic agent;
   heating the hydroxyapatite coated implant and solution to a temperature of about 60° C. to about 100° C.; and
   applying pressure to the hydroxyapatite coated implant and solution of about 2 bar to about 10 bar to load the hydroxyapatite coated implant with the therapeutic agent for improved therapeutic agent delivery at an implant site.

2. The method according to claim 1, wherein the implant is a device selected from the group consisting of fixation pins, orthopedic devices, dental implants, stents, drug delivery devices, sheets, films, meshes, soft tissue implants, implantable electrodes, implantable sensors, drug delivery pumps, tissue barriers and shunts.

3. The method according to claim 1, wherein the implant includes a surface metal coating selected from the group consisting of $TiO_2$, TiO, $TiCrO_2$, $TiO_3$, $Ti_3O_5$, $SiO_2$, $MgO_2$, $AlO_2$, and $CrO_2$.

4. The method according to claim 1, wherein the implant has a base metal of Titanium and Stainless Steel alloys and a surface coating selected from the group of $TiO_2$, TiO, $TiCrO_2$, $Ti_2O_3$, $Ti_2O_5$, $SiO_2$, $MgO_2$, $AlO_2$, and $CrO_2$.

5. The method according to claim 4, further comprising the step of coating the implant with the surface coating prior to applying the hydroxyapatite coating.

6. The method according to claim 1, wherein the therapeutic agent is selected from the group consisting of antibiotics, vitamins, chemotherapy drugs, bisphosphonates, strontium-ranelate, PTH, osteoporotic drugs, growth factors, and a combination thereof.

7. The method according to claim 1, wherein the implant is a material selected from the group consisting of titanium, titanium alloy, nickel-titanium alloy, tantalum, platinum-iridium alloy, gold, magnesium, stainless steel, chromo-cobalt alloy, ceramics, biocompatible plastics or polymers and combinations thereof.

8. The method according to claim 1, wherein the hydroxyapatite coating is grown biomimetically.

9. The method according to claim 8, wherein the thickness of the biomimetic hydroxyapatite coating deposited is of about 1 μm to about 10 μm.

10. The method according to claim 1, wherein the coating is an ion substituted hydroxyapatite.

11. The method according to claim 1, wherein the thickness of the hydroxyapatite coating deposited is of about 1 μm to about 10 μm.

12. The method according to claim 1, wherein the step of contacting the hydroxyapatite coated implant with the solution uses a solution of 20 mg or greater of therapeutic agent per ml of solution.

13. The method of according to claim 1, wherein the therapeutic agent has a penetration depth of about 0.5 µm to about 8 µm.

14. A method for loading a hydroxyapatite coated implant with a therapeutic agent, comprising:
providing an implant;
coating the implant with a metal selected from the group consisting of $TiO_2$, TiO, $TiCrO_2$, $Ti_2O_3$, $Ti_3O_5$, $SiO_2$, $MgO_2$, $AlO_2$, and $CrO_2$;
applying a hydroxyapatite coating on a surface of the implant;
thereafter placing the hydroxyapatite coated implant in a solution including the therapeutic agent;
heating the hydroxyapatite coated implant and the solution to a temperature of about 60° C. to about 100° C.; and
applying pressure to the hydroxyapatite coated implant and solution of about 2 bar to about 10 bar to load the hydroxyapatite coated implant with the therapeutic agent for improved therapeutic agent delivery at an implant site; and
thereafter removing the implant from the solution after about 5 minutes.

15. The method according to claim 14, wherein the implant is a device selected from the group consisting of fixation pins, orthopedic devices, dental implants, stents, drug delivery devices, sheets, films, meshes, soft tissue implants, implantable electrodes, implantable sensors, drug delivery pumps, tissue barriers and shunts.

16. The method according to claim 14, wherein the therapeutic agent is selected from the group consisting of antibiotics, vitamins, chemotherapy drugs, bisphosphonates, strontium-ranelate, PTH, osteoporotic drugs, growth factors, and a combination thereof.

17. The method according to claim 14, wherein the implant is a material selected from the group consisting of titanium, titanium alloy, nickel-titanium alloy, tantalum, platinum-iridium alloy, gold, magnesium, stainless steel, chromo-cobalt alloy, ceramics, biocompatible plastics or polymers and combinations thereof.

18. The method according to claim 14, wherein the hydroxyapatite coating is grown biomimetically.

19. The method according to claim 18, wherein the thickness of the biomimetic hydroxyapatite coating deposited is of about 1 µm to about 10 µm.

20. The method according to claim 14, wherein the hydroxyapatite coating contains ions selected from the group consisting of calcium, phosphates, fluorine, strontium, silicon, and magnesium.

21. A method for loading a hydroxyapatite coated implant with a therapeutic agent, comprising the steps of:
providing an implant;
applying a hydroxyapatite coating on a surface of the implant;
contacting the hydroxyapatite coated implant with a solution including the therapeutic agent;
heating the hydroxyapatite coated implant and solution to a temperature of about 60° C. to about 100° C.; and
applying pressure to the hydroxyapatite coated implant and solution of about 2 bar to about 10 bar to load the hydroxyapatite coated implant with the therapeutic agent for improved therapeutic agent delivery at an implant site; and
thereafter removing the implant from the solution after about 5 minutes.

* * * * *